United States Patent [19]

Hernestam et al.

[11] 4,070,473

[45] Jan. 24, 1978

[54] PIPERIDINO-BUTYROPHENONES

[75] Inventors: Sven Eric Harry Hernestam; Bengt Eric Sigvard Kjellberg; Knut Gunnar Olsson, all of Malmo, Sweden

[73] Assignee: AB Ferrosan, Malmo, Sweden

[21] Appl. No.: 633,268

[22] Filed: Nov. 19, 1975

Related U.S. Application Data

[63] Continuation of Ser. No. 435,842, Jan. 23, 1974, abandoned.

[30] Foreign Application Priority Data

Jan. 26, 1973 United Kingdom ............... 4246/73

[51] Int. Cl.$^2$ ............................................ C07D 211/48
[52] U.S. Cl. ................................... 424/267; 260/293.8
[58] Field of Search ....................... 260/293.8; 424/267

[56] References Cited

U.S. PATENT DOCUMENTS 3,424,755   1/1969   Denss et al. ...................... 260/293.8

FOREIGN PATENT DOCUMENTS 18,877    9/1972   Japan ............................... 260/293.8
478,120  10/1969   Switzerland ...................... 260/293.8

OTHER PUBLICATIONS

P.A.J. Janssen, Intern. Jour. Neuropharmacol., (1962), vol. 1, pp. 145–148.

*Primary Examiner*—Norma S. Milestone
*Attorney, Agent, or Firm*—Gordon W. Hueschen

[57] ABSTRACT

Novel gamma-(4-lower-alkyl-4-lower-alkoxypiperidino)-p-fluorobutyrophenones and acid addition salts thereof, useful as central depressants, e.g., neuroleptics (antipsychotics). Pharmaceutical compositions thereof and method of treating therewith.

5 Claims, 1 Drawing Figure

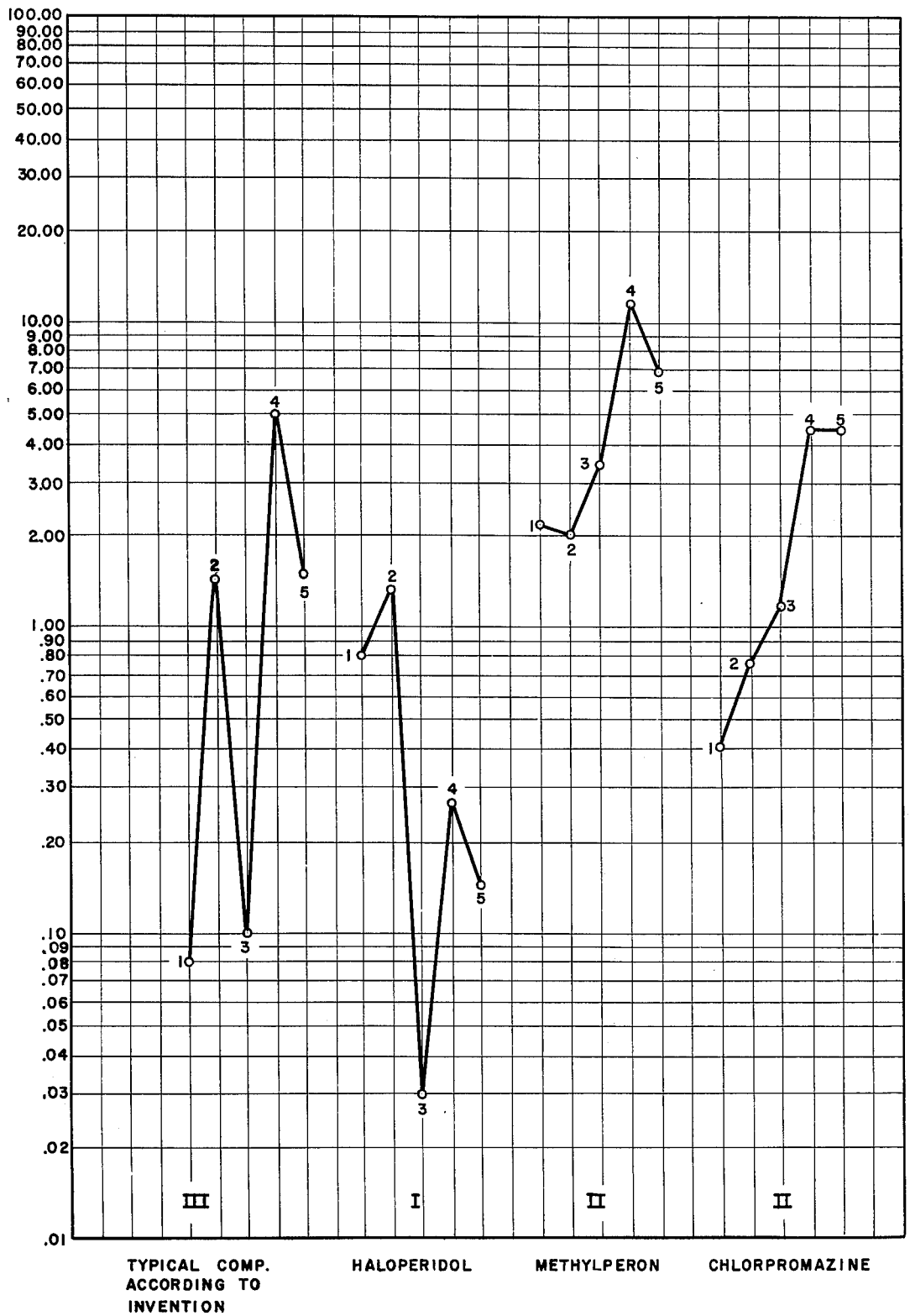

PIPERIDINO-BUTYROPHENONES

This is a continuation of application Ser. No. 435,842, filed Jan. 23, 1974, now abandoned.

BACKGROUND OF INVENTION

1. Field of Invention gamma-Piperidino-butyrophenones; central depressant, neuroleptic compounds.

2. Prior Art

A number of ketones of the general formula

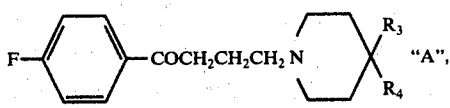

wherein $R_3$ and $R_4$ are widely different groups, have been made and tested.

Janssen (Cavallito; "Structure-Activity Relationships I", page 37) has stated that one of the groups $R_3$ and $R_4$ must be aromatic and that only one may be hydrogen if the ketone is to be an antipsychotic.

For comparison with the compounds of the present invention, we have used two clinically-established piperidino ketones, namely: Haloperidol, wherein

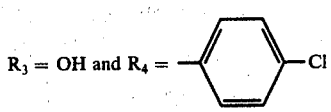

and

Methylperon, wherein $R_3 =$ H and $R_4 =$ $CH_3$.

Several compounds having the above-mentioned general formula have also been described in the literature as having, for instance, tranquilizing, central blocking, analgetic, antipyretic, and antiphlogistic properties.

In that context, for instance, compounds are described wherein:

$R_3 =$ OH or acyloxy and $R_4 =$ lower alkyl. (See Brit. pat. 1,131,534; Jap. pat. appl. 4,718,877.)

However, the established clinically-useful compounds of the prior art have pronounced shortcomings and side-effects, and there is a clear demand for more specific and advantageous compounds in this activity and utility area, especially as neuroleptics (anti-psychotics). The fulfillment of this demand is one of the objects of the present invention, as further elucidated hereinafter.

SUMMARY OF THE INVENTION

This invention relates to novel basic ketones, a process for their preparation, pharmaceutical compositions thereof, and method of treating therewith.

The compounds provided by the present invention are selected from the group consisting of (a) basic ketones having the general formula

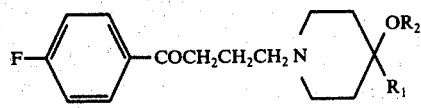

wherein $R_1$ and $R_2$ each represents a straight or branched alkyl group having one to five carbon atoms, inclusive, and b. acid addition salts thereof These novel gamma-piperidino-butyrophenones have valuable pharmacological properties, especially central depressant effects, which makes them useful as neuroleptics (i.e., antipsychotically active substances).

OBJECTS

It is an object of the present invention to provide novel gamma-(4-lower-alkyl-4-lower-alkoxypiperidino)-p-fluorobutyrophenones and acid addition salts thereof, which are useful as central depressants, e.g., neuroleptics (antipsychotics), a process for producing the same, pharmaceutical compositions thereof, and a method of treating psychotic states therewith. Additional objects will become apparent hereinafter, and still others will be obvious to one skilled in the art.

PREPARATION:

According to the present invention, the novel ketones of general Formula I are prepared: a. by reacting a 4-alkyl-4-alkoxypiperidine of the general formula

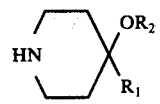

with a butyrophenone of the formula

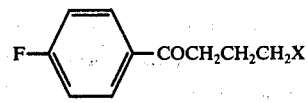

wherein X is halogen (Cl, Br, I) or a sulfonic acid radical

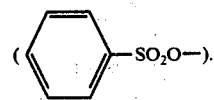

Other processes may also be employed, e.g., inter alia:

b. 1. a ketoamide of the formula

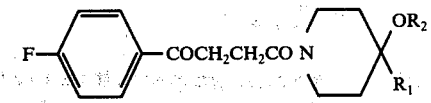

is reduced to the alcohol

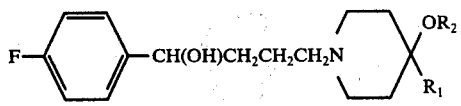

which is oxidized to I. b. 2. a ketoamide according to b 1. with the keto group protected

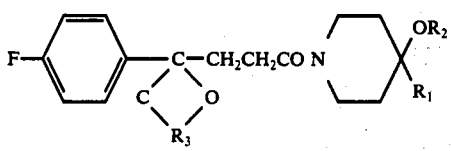

wherein R₃ is a methylene chain, possibly substituted with one or more methyl groups, e.g.,

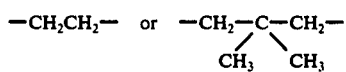

is reduced to

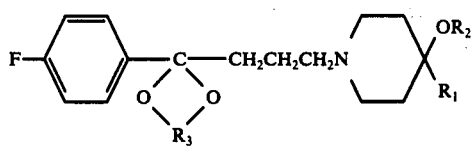

whereupon this compound is hydrolyzed to I. b. 3. p-Fluorobenzaldehyde is reacted with a metalorganic compound of the general formula

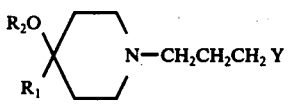

wherein Y is —Mg hal (Cl, Br, I) or Li, whereupon the obtained alcohol II is oxidized to I. c. 1. a metalorganic compound of the formula

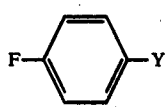

wherein Y is Mg hal (Cl, Br, I) or Li is reacted with a piperidinoderivative of the formula

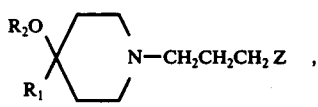

wherein Z is a carboxylic group or a derivative thereof (nitrile, acid halide, or ester), whereupon the obtained product is hydrolyzed to I. c. 2. the compound

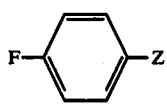

is reacted with a metalorganic compound of the formula

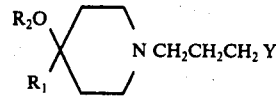

wherein Y and Z have the meanings hereinbefore defined, whereupon the obtained compound is hydrolyzed to I.

d. a compound of the formula

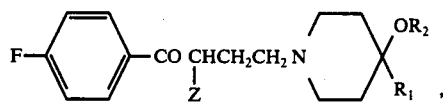

in which Z is as hereinbefore defined, is hydrolyzed and decarboxylated to I. e. in a compound of the general formula

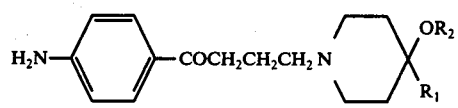

the amino group is converted to F by standard procedure for such replacement.

In the foregoing reactions a – e, R₁ and R₂ have the meanings hereinbefore defined (in Formula I). Of the described synthetic methods, method a) is the method of choice because the starting products are inexpensive and readily manufactured and because the synthesis can be performed with good yields to give pure end products.

The starting 4-methyl-4-methoxypiperidine is synthesized according to Manus et al., J. Med. Chem. 8, 766 (1965). The other 4-lower-alkyl-4-loweralkoxypiperidine starting materials are prepared in exactly the same manner from the appropriate starting materials, which are known.

The selected substituted piperidine is reacted with the selected p-fluoro-gamma-halogen-butyrophenone, preferably in a suitable non-polar solvent, e.g., benzene, toluene, or xylene. If a polar solvent is employed, dimethylformamide is preferred. The reaction is preferably performed using an excess of the piperidine or in the presence of an acid binding agent, e.g., triethylamine or potassium carbonate. The reaction can additionally be carried out in the presence of potassium iodide, whereby undesired side reactions are avoided. After the reaction is complete, the product is generally treated with water or aqueous alkali and the thusformed basic ketone is extracted with ether. From the dried ether-solution, the hydrochlorides are precipitated with hydrochloric acid. The hydrochlorides are readily recrystallized from, e.g., ethanol-ether, acetone-ether, methylethylketone, ethylacetate, and like solvents or solvent mixtures.

After completion of other reactions which may also be employed for their production, isolation of the basic ketone is carried out in the same manner.

The novel compounds of the invention are thus usually obtained as an acid addition salt thereof, e.g., their hydrochloride. Other pharmaceutically acceptable addition salts can be prepared from the hydrochloride via the base, or directly from the base.

The compounds of the invention are most conveniently employed as pharmaceuticals in the form of water-soluble, non-toxic acid-addition salts. Although the non-toxic salts are preferred, any salt may be prepared for use as a chemical intermediate, as in the preparation of another but non-toxic acid-addition salt. The free basic compounds of Formula I may be conveniently converted to their acid addition salts by reaction of the free base with the selected acid, preferably in the presence of an organic solvent inert to the reactants and reaction products under the conditions of the reaction. The acids which can be used to prepare the preferred non-toxic acid addition salts are those which produce, when combined with the free bases, salts the anions of which are relatively innocuous to the animal organism in therapeutic doses of the salts, so that beneficial physiological properties inherent in the free bases are not vitiated by side-effects ascribable to the anions. Appropriate acid-addition salts are those derived from mineral acids such as hydrochloric, hydrobromic, hydroiodic, nitric, sulfuric, methanesulfonic, isothionic, sulfamic, phosphoric, and organic acids such as acetic, citric, lactic, fumaric, propionic, maleic, oxalic, benzoic, and tartaric. The preferred acid addition salt is the hydrochloride.

The acid-addition salts are prepared either by dissolving the free base in an aqueous solution containing the appropriate acid and isolating the salt by evaporating the solution, or by reacting the free base and the selected acid in an organic solvent, in which case the salt ordinarily separates directly or can be conventionally recovered by concentration of the solution or the like. Conversely the free base may be obtained conventionally by neutralizing the acid-addition salt with an appropriate base such as ammonia, ammonium hydroxide, sodium carbonate or the like, extracting the liberated base with a suitable solvent, illustratively ethyl acetate or benzene, drying the extract, and evaporating to dryness of fractionally distilling, or in other conventional manner.

DETAILED DESCRIPTION OF THE INVENTION

The following preparations and examples are given by way of illustration only, and are not to be construed as limiting. Preparation of 4-alkyl-4-alkoxy-piperidines of the formula

Preparation A wherein $R_1$ and $R_2$ are alkyl with 1–5 carbon atoms.

The piperidines used in ex. 1–16 are prepared according to Manus et al. J. Med. Chem. 8, 766 (1965).

1-Benzyl-4-piperidone is treated with alkylmagnesiumbromide ($R_1MgBr$) or alkyllithium ($R_1Li$) and the 1-Benzyl-4-alkyl($R_1$)-4-hydroxy piperidine formed is alkylated in known manner, whereupon the benzylgroup is removed by catalytic reduction.

Preparation B wherein $R_1$ is alkyl with 1–5 carbon atoms and $R_2$ alkyl with 3–5 carbon atoms. The following modification of the methods is preferred.

Preparation of 4-methyl-4-butoxy-piperidine (No. 4 in the table)

a. 10-Benzyl-1.6-dioxa-11-aza-spirododecane

1-Benzyl-4-piperidino and butane-1.4-diol are reacted in chloroform, saturated with HCl to produce compound a). B.p. 110°–115° C/0.01 mm Hg. M.p. 51°–53° C.

b. 4-[(-Benzyl-4-methyl-4-piperidyl)oxy]butanol

Compound a) is added to methylmagnesiumiodide to produce compound b). B.p. 120°–127° C/0.01 mm Hg.

c. 4-[(1-Benzyl-4-methyl-4-piperidyl)oxi]butylchloride

Compound b) is chlorinated by thionylchloride to produce compound c). B.p. 118°–120° C/0.01–2 mm Hg. The melting point of the hydrochloride is 173°–175° C.

d. 1-Benzyl-4-methyl-4-butoxypiperidine

Compound c) is reduced with lithium aluminum hydride in tetrahydrofuran to compound produce d). B.p. 88°–90° C/0.01 mm Hg.

e. 4-Methyl-4-butoxypiperidine

The benzylgroup in 1-Benzyl-4-methyl-4-butoxy-piperidine is removed in known manner as described in the literature.

Summary of starting 4-alkyl-4-alkoxypiperidines

| NO. | $R_1$ | $R_2$ | M.p. ° C hydrochloride | (B.p. ° C) mm Hg |
|---|---|---|---|---|
| 1 | CH₃ | CH₃ | 180–181 | |
| 2 | SAME AS IN EXAMPLES 2–14, Following. | | 118 | 62–63/10 |
| 3 | " | | | 63–65/11 |
| 4 | " | | | 78–81/10–11 |
| 5 | " | | 146–147 | |
| 6 | " | | 117 | 77–78/10 |
| 7 | " | | | 81–84/10 |
| 8 | " | | 128–130 | |
| 9 | " | | 131–132 | |
| 10 | " | | 194–196 | |
| 11 | " | | | 93–95/11–12 |
| 12 | " | | 123–125 | |
| 13 | " | | | 126–129/14–15 |
| 14 | " | | | 99–103/12–14 |

Example 1 gamma-(4-methyl-4-methoxy-piperidino)-p-fluorobutyrophenone

A solution of 20.1 g (0.1 m) of gamma-chloro-p-fluorobutyrophenone, 30 g (0.2 m) of 4-methyl-4-methoxy-piperidine and 0.1 g. of potassium iodide in 150 ml of toluene is heated in a glass autoclave for 15 hours at 100°–110° C. The KI and the 4-methyl-4-methoxy-piperidine hydrochloride formed in the reaction are separated by filtration and the solvent removed from the filtrate by evaporation under a vacuum on a steam bath. The obtained base is dissolved in ether and the hydrochloride is precipitated with alcoholic HCl. The reaction product is purified by recrystallization from ethanol-ether. Yield 22 g. Melting point 182° C.

EXAMPLES 2-14

Proceeding generally as described in Example 1, further compounds according to the invention enumerated in the following table are prepared.

for two hours and the obtained mixture decomposed with water. The precipitate is filtered off and the ether solution evaporated. The residue, which consists of the alcohol corresponding to the butyrophenone, is oxidized according to Oppenauer with 60 g of aluminum- $$F-\text{C}_6\text{H}_4-COCH_2CH_2CH_2-N\begin{pmatrix}OR_2\\R_1\end{pmatrix}, HCl$$

| NO. | R$_1$ | R$_2$ | M.p. °C | B.p. of the base °C/mm Hg |
|---|---|---|---|---|
| 2 | CH$_3$ | CH$_2$CH$_3$ | 163–164 | |
| 3 | CH$_3$ | CH$_2$CH$_2$CH$_3$ | 158–159 | |
| 4 | CH$_3$ | CH$_2$CH$_2$CH$_2$CH$_3$ | 167–168 | 124–130/0.01 |
| 5 | CH$_2$CH$_3$ | CH$_3$ | 200 | |
| 6 | CH$_2$CH$_3$ | CH$_2$CH$_3$ | 176–177 | 130–135/0.01 |
| 7 | CH$_2$CH$_3$ | CH$_2$CH$_2$CH$_3$ | 167–169 | |
| 8 | CH$_2$CH$_2$CH$_3$ | CH$_3$ | 174–175 | |
| 9 | CH$_2$CH$_2$CH$_3$ | CH$_2$CH$_3$ | 149–152 | |
| 10 | CH(CH$_3$)$_2$ | CH$_3$ | 190–191 | |
| 11 | CH$_2$CH$_2$CH$_2$CH$_3$ | CH$_3$ | 175–176 | |
| 12 | CH$_2$CH$_2$CH$_2$CH$_3$ | CH$_2$CH$_3$ | 168–171 | |
| 13 | CH$_2$CH$_2$CH$_2$CH$_2$CH$_3$ | CH$_2$CH$_3$ | 136–138 | |
| 14 | CH$_3$ | CH$_2$CH$_2$CH$_2$CH$_2$CH$_3$ | — | 128–132/ 0.005–0.01 |

EXAMPLE 15

Preparation of gamma-(4-ethyl-4-ethoxypiperidino)-p-fluoro-4-butyrophenone hydrochloride To a Grignard solution prepared from 70.0 g (0.4 m) of p-fluorobromo-benzene and 9.8 g (0.4 m) of magnesium in 500 mls. of ether, 22.4 g (0.1 m) of gamma-(4-ethyl-4-ethoxy-piperidino) butyronitrile dissolved in 200 mls. of ether was added dropwise. After the addition was complete, the reaction mixture was refluxed for seven hours, whereupon water and finally a saturated ammonium chloride solution was added for decomposition of the reaction mixture. The ether phase was separated and evaporated in vacuo. To the residue 500 mls. of 5 N hydrochloric acid was added, and the mixture then refluxed for twenty hours. After cooling, an excess of concentrated ammonia was added and the reaction mixture was extracted with ether. The ether solution was evaporated in vacuo and the residue was distilled. 26 g of the compound was obtained at 130°–135° C/0.01 mms. of Hg.

The hydrochloride was prepared in the manner of Example 1. Melting point 176°–177° C. The hydrobromide is prepared in the same manner, using hydrogen bromide in place of hydrogen chloride. The citrate is prepared using citric acid.

EXAMPLE 16

Preparation of gamma-(4-isopropyl-4-methoxy-piperidino)-p-fluorobutyrophenone hydrochloride To a mixture of 21.5 g (0.1 m) of gamma-(p-fluorophenyl)-gamma-oxo-butyric acid chloride and 15.7 (0.1 m) of 4-isopropyl-4-methoxy-piperidine in 200 ml of benzene, 15.5 ml (0.11 m) of triethylamine is added. The triethylamine hydrochloride formed is filtered off and the solvent removed by evaporation under vacuum on a steambath. The residue is dissolved in dry ether and added dropwise to a suspension of 15 g of lithium aluminum hydride in ether. The reaction mixture is refluxed isopropylate in 500 ml of dry acetone. The reaction mixture is refluxed for 12 hours, cooled, and decomposed with water. After centrifugation, the solution is evaporated to dryness, whereafter the residue dissolved in ether and the hydrochloride precipitated with alcoholic hydrochloric acid. After recrystallization, the hydrochloride melts at 190°–192° C. Yield 19 g. The tartrate is prepared using tartaric acid.

EXAMPLE 17

Preparation of gamma-(4-methyl-4-butoxypiperidino)-p-fluorobutyrophenone hydrochloride 3.1 g (0.127 m) of sodium is granulated in 200 ml of boiling toluene. After cooling, 26.5 g (0.126 m) of ethyl beta-(p-fluorophenyl)-beta-oxopropionate is added drop by drop and then the solution is stirred for one-half hour at 50° C. The yellow solution which forms is cooled and 30 g (0.30 m) of beta-(4-methyl-4-butoxy-piperidino)-ethyl-chloride is added rapidly thereto. The reaction mixture is stirred for four hours at 60° C and for five hours at 85° C. After evaporation on a steam bath and addition of 500 ml of 2.5-N sulphonic acid, the solution is refluxed for sixteen hours, cooled, alkalized with an excess of potassium carbonate, and extracted with ether. The solution is evaporated and the residue distilled at 124–130/0.01 mm Hg. Yield 19.5 g. The hydrochloride has the m.p. 167°–169° C.

PHARMACOLOGY, COMPOSITIONS, AND USE

Even if it should be possible to predict some kind of activity in butyrophenones having the foregoing formula "A", it has been and still is accepted in the art that it is necessary to use a series of established pharmacological tests in order to establish the "pharmacological profile" of a neuroleptically active compound. For that reason we have carried out a series of tests, which are especially suited for the evaluation of new piperidinobutyrophenones, but which are also useful for comparison of new compounds with other compounds having the same field of application.

In the following series of tests, we have compared the new ketones of the present invention with the following:

Haloperidol — formula hereinbefore mentioned ($R_3 =$ OH; $R_4 =$ p-chlorophenyl)

Methylperon — formula hereinbefore mentioned ($R_3 =$ H; $R_4 = CH_3$) chlorpromazine

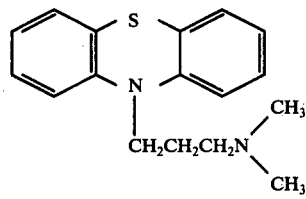

in each of the following established standard tests:
1. Inhibition of aggressive behaviour in male mice.
2. Inhibition of climbing in mice (inhibition of exploratory behaviour).
3. Amphetamine antagonism in rats (antipsychotic effect).
4. Cataleptogenic effect in rats (measure of the extrapyramidal side effects).
5. Inhibition of conditioned behaviour in rats. These tests were in accord with published test procedures and protocols, for instance:
1. Valzelli, L. in Aggressive Behaviour, Eds. Garattini and Sigg, p. 70 (1969)
2. Sandberg, S. in Arzneimittelforschung, 9, 203 (1958)
3. Randrup, A. et al. in Acta Pharmacol. (Kph), 20, 145 (1963)
4. Stille, G. in Schweiz. Med. Wochenschrift, 99, 1645 (1969)
5. Jacobsen and Sonne in Acta Pharmacol. & Toxicol., 11, pp. 135-147 (1955)

On comparison of these test results from the Table, it is possible to separate the compounds into three groups, all of which show a pattern of neuroleptic activity, but which are in fact characterized by importantly different "pharmacological profiles". See the Table and FIG. 1.

Group II Example: Chloropromazine, Methylperon

Their profiles are characteristic of high-dosed unspecifically sedative neuroleptics. Methylperon is not very active in Tests 1 and 3. Chlorpromazine is not very active in Test 3.

Group III Example: New ketones with Formula I

These compounds have considerably lower extrapyramidal effect than compounds from Group I. The new compounds are specifically antiaggressive (Table-Test No. 1) anti-psychotic, and have an anxiolytic effect (Table-Test No. 3). The cardiovascular effects are insignificant.

Up to the present time, such favorable neuroleptic profiles have not been described for any compound in this area.

The antipsychotic effect as shown in Test No. 3 is further confirmed by the blocking of apomorphine emesis in dogs. Ref: Janssen, P. A. J. et al. Arzneimittelforschung, 1, 1196 (1965) Furthermore, the compounds have a pronounced serotonine inhibiting effect, Ref: Alps, J. et al. Br. J. Pharmac. 44, 52 (1972) and a strong anti-inflammatory effect (measured with carrageenin-induced edema in rats). Ref: Takashima, T. et al. Arzneimittelforschung 22, 711 (1972) Their toxicity is rather low, 200 - 300 mg/kg. In comparison, the toxicity for haloperidol is 70 mg/kg and for methylperon is 280 mg/kg (all toxicities being performed subcutaneously on mice).

In view of their unusual properties, the novel compounds of the present invention are also suited for treatment of mental disturbances in humans, for instance schizophrenic, manic, anxious and agony states. Their general properties as tranquilizers also make the new compounds suitable for veterinary applications. the present invention has been evidenced by tests in lower animals and representative of these are reported herein.

In their most advantageous form, the compositions of the present invention will contain a non-toxic pharmaceutical carrier in addition to the active ingredient. Exemplary carriers are: solids-lactose, magnesium stearate, calcium stearate, starch, terra alba, dicalcium phosphate, sucrose, talc, stearic acid, gelatin, agar, pec-

| TEST Compound of Example | 1. Inhibition of agression, mice ED50 mg/kg s.c. | 2. Inhibition of exploratory behaviour, mice ED50 mg/kg s.c. | 3. Amphetamine antagonism, rats ED50 mg/kg s.c. | 4. Cataleptogenic effect, rats ED50 mg/kg s.c. | 5. Inhibition of conditioned avoidance response rats ED50 mg/kg s.c. |
|---|---|---|---|---|---|
| 1 | 0.20 | 0.65 | 0.35 | 10.0 | 0.6 |
| 2 | 0.70 | 1.00 | 0.10 | 6.0 | 1.3 |
| 3 | 0.35 | 1.00 | 0.20 | 7.0 | 0.5 |
| 4 | 0.35 | 2.00 | 0.75 | 20.0 | 2.5 |
| 5 | 0.70 | 0.70 | 0.10 | 10.0 | 1.5 |
| 6 | 0.08 | 1.40 | 0.10 | 5.0 | 1.5 |
| 7 | 0.70 | 1.20 | 0.35 | 6.0 | |
| 8 | 0.50 | 3.10 | 1.00 | 6.2 | 5.5 |
| 10 | 0.15 | 1.10 | 0.10 | 5.0 | 1.2 |
| 12 | 0.35 | 1.60 | 0.07 | 3.0 | 5.0 |
| 13 | 0.50 | 1.30 | 0.35 | 6.8 | |
| Haloperidol | 0.80 | 1.30 | 0.03 | 0.27 | 0.15 |
| Methylperon | 2.20 | 2.00 | 3.50 | 12.00 | 6.80 |
| Chlorpromazine | 0.40 | 0.75 | 1.20 | 4.50 | 4.50 |

Group I Example: Haloperidol

The profile is characteristic of low-dosed specific neuroleptics. Their great disadvantage is their extrapyramidal side effects [demonstrated by a pronounced cataleptogenic effect in rats (Table-Test No. 4)].

tin, acacia, or the like; liquids — peanut oil, sesame oil, olive oil, water, or the like. The active agents of the invention can be most conveniently administered in such compositions containing about 0.01 to 67 percent, preferably 0.04 to 12.15 percent, by weight of the active ingredient. Such formulations are illustrated in U.S. Pat. No. 3,402,244.

A wide variety of pharmaceutical forms suitable for many modes of administration and dosages may be employed. For oral administration the active ingredient and pharmaceutical carrier may, for example, take the form of a granule, pill, tablet, lozenge, or liquid suspension; for parenteral administration, the composition may be a sterile solution; and for rectal administration, a suppository.

The method of using the compounds of the present invention comprises internally administering a compound of Formula I, usually in the form of a non-toxic, pharmacologically acceptable acid-addition salt, and preferably admixed with a pharmaceutical carrier, for example, in the form of any of the above-mentioned compositions, or filled into a capsule, to alleviate psychotic conditions and symptoms thereof in a living animal body. The compounds and their non-toxic salts, especially the hydrochlorides, may be advantageously employed in amounts approximating those employed for any of the three clinically-useful compounds used for comparative testing as reported herein. Illustratively, they may be used in an amount of from about 0.1 to 200 milligrams per unit dose, preferably from about 2.5 to 50 milligrams for an oral dose, while parenteral dosages are usually less and ordinarily about one-half the oral dose so that the preferred parenteral unit dosage will be about one to 25 milligrams. The unit dose is preferably given a suitable number of times daily so that the daily dose may vary from 0.3 to 600 milligrams. Preferred daily dosages will vary from about 7.5 to 150 milligrams (oral) to about three to 75 milligrams (parenteral). However, these compounds are subject to wide variations in optimum daily and unit dosages, and the invention should therefore not be limited by the exact ranges stated. The exact dosage, both unit and daily, will of course have to be determined according to established medical principles. In addition, the active ingredients of the present invention or compositions containing the same may either be administered together with or include other physiologically active materials and/or medicaments, e.g., buffering agents, antacids, sedatives, stimulants, anticholinergics, analgesics, or the like.

The following formulations are representative for all of the pharmacologically active compounds of the invention, but have been particularly designed to embody as active ingredient gamma-(4-methyl or ethyl-4-methoxy or ethoxypiperidino)-p-fluoro-butyrophenone, and especially a pharmacologically acceptable salt thereof, for example its tartrate, hydrochloride, hydrobromide, fumarate, or like pharmacologically acceptable salt.

For oral use the compounds are usually administered as tablets, although other forms may be employed. Tablets may be made by compounding one of the compounds of the invention, preferably as an acid-addition salt, with customary carriers and adjuvants, e.g., talc, magnesium stearate, starch, lactose, gelatine, gums, or the like.

The following is a suitable tablet formulation:

0.1 – 1g of gamma-(4-ethyl-4-ethoxypiperidino)-p-fluorobutyrophenone hydrochloride
9 g of potato starch
1 g of colloidal silica
2 g of talc
0.2 g of magnesium stearate
2.5 g of 5% aqueous solution of gelatine.

This mixture is made up into 100 tablets, containing 1-10 mg of the active component.

The hydrochlorides or other acid addition salts are readily soluble in water, which makes them particularly useful, since it enables the new compounds to be administered parenterally by injection.

For injection, the following solution is suitable:

5 - 500 mg of gamma-(4-methyl-4-methoxypiperidino)-p-fluoro-butyrophenone hydrochloride dissolved in 100 ml of water containing 0.6 g of NaCl. The resulting solution is filled into ampoules; each contain 2 ml of solution and thus 0.1–10 mg of the active compound. They are sterilized in the usual manner.

The pharmacologically active compounds provided by the present invention may also be administered successfully by embodying an effective quantity thereof in an injectable emulsion or suspension for injection into an animal body, in oral powders, suspension or syrups, and in other acceptable dosage forms.

Although very small quantities of the active materials of the present invention are effective when minor therapy is involved or in cases of administration to subjects having a relatively low body weight, unit dosages are usually five milligrams or above and preferably twenty-five, fifty or one-hundred milligrams or even higher, depending of course upon the emergency of the situation and the particular result desired. The exact individual dosages as well as daily dosages in a particular case will of course be determined according to established medical principles and under the supervision of the physician or veterinarian involved.

Various modifications in the compounds, compositions, and methods of the invention will be apparent to one skilled in the art and may be made without departing from the spirit or scope thereof, and it is therefore to be understood that the invention is to be limited only by the scope of the appended claims.

We claim:

1. Gamma-(4-ethyl-4-ethoxypiperidino)-p-fluoro-butyrophenone or a pharmaceutically-acceptable acid addition salt thereof.

2. Gamma-(4-ethyl-4-ethoxy-piperidino)-p-fluoro-butyrophenone.

3. Gamma-(4-ethyl-4-ethoxy-piperidino)-p-fluoro-butyrophenone hydrochloride.

4. A pharmaceutical composition suitable for use in the alleviation of aggressive states, or for tranquilization of a subject in need thereof, comprising a compound of claim 1, in an amount effective for said purpose, in association with a pharmaceutical carrier.

5. Method for the treatment of a subject in need of alleviation of an aggressive state, or in need of tranquilization, comprising administering to the subject a compound of claim 1 in an amount effective for said purpose.

* * * * *

UNITED STATES PATENT OFFICE
CERTIFICATE OF CORRECTION

Patent No. 4,070,473  Dated Jan. 24, 1978

Inventor(s) Sven Eric Harry Hernestam et al

It is certified that error appears in the above-identified patent and that said Letters Patent are hereby corrected as shown below:

Col. 5, line 65: "alkylithium" should read --alkyllithium--

Col. 7, line 13: "$CH_2 / CH_3$" should read --$CH_2CH_3$--

Col. 10, line 36: after "application." insert --The high order of activity of the active agents of-- as the beginning of a new paragraph.

*Signed and Sealed this*

*Sixth* Day of *June 1978*

[SEAL]

*Attest:*

RUTH C. MASON
*Attesting Officer*

DONALD W. BANNER
*Commissioner of Patents and Trademarks*